United States Patent
Olson et al.

(10) Patent No.: US 8,029,730 B1
(45) Date of Patent: Oct. 4, 2011

(54) FLOW CELL FOR CHEMILUMINESCENCE ANALYSIS

(75) Inventors: Don C. Olson, Gig Harbor, WA (US); Duane K. Wolcott, Fox Island, WA (US); Graham D. Marshall, Fox Island, WA (US)

(73) Assignee: Global FIA, Inc., Fox Island, WA (US)

( * ) Notice: Subject to any disclaimer, the term of this patent is extended or adjusted under 35 U.S.C. 154(b) by 114 days.

(21) Appl. No.: 12/540,854

(22) Filed: Aug. 13, 2009

(51) Int. Cl.
*G01N 21/76* (2006.01)
*G01N 21/00* (2006.01)
*G01N 21/64* (2006.01)
*G01T 1/10* (2006.01)

(52) U.S. Cl. .............. 422/52; 422/82.05; 422/82.07; 422/82.08; 436/172; 250/361 C; 356/246

(58) Field of Classification Search .......... None
See application file for complete search history.

(56) References Cited

U.S. PATENT DOCUMENTS

| | | | |
|---|---|---|---|
| 3,679,312 A | 7/1972 | Mansberg | |
| 4,841,151 A | 6/1989 | Shope | |
| 5,416,576 A | 5/1995 | Westlake, III et al. | |
| 5,451,788 A | 9/1995 | Pollack | |
| 5,559,324 A | 9/1996 | Rapkin et al. | |
| 5,644,395 A | 7/1997 | Folta | |
| 5,856,670 A * | 1/1999 | Rapkin et al. | 250/252.1 |
| 6,537,501 B1 | 3/2003 | Holl et al. | |
| 6,716,391 B1 | 4/2004 | Olson | |
| 2003/0175947 A1 | 9/2003 | Liu et al. | |

* cited by examiner

*Primary Examiner* — Jill Warden
*Assistant Examiner* — Neil N Turk
(74) *Attorney, Agent, or Firm* — Reginald F. Roberts, Jr.

(57) ABSTRACT

A flow cell for chemiluminescence analysis. The flow cell has a flat, thin, opaque plate, with a groove machined into one side of the plate. An inlet port at the center, and an outlet port at the outside end of the groove pass through the plate, which is sandwiched between a flat sapphire window and a cell cap of a housing. The groove side faces the sapphire window, forming a flow channel with one wall being the sapphire window. A light detector is inserted into the housing until it butts up against that part of the housing holding the sapphire window, placing it very close to the generated light. The other side of the plate mates with inlet and outlet ports of the housing cap.

6 Claims, 10 Drawing Sheets

FLOW CELL FOR CHEMILUMINESCENCE ANALYSIS

BACKGROUND OF THE INVENTION

The present invention relates to chemical analysis. More particularly, the invention relates to a flow cell for use with flow-based chemiluminescence measurements.

Chemiluminescence is the generation of light from chemical reactions. Chemiluminescence processes have attracted mankind's attention for centuries. Aristotle wrote the first known report on the phenomenon when he noted that weak light was emitted by dead fish and fungi. The term chemiluminescence was first defined by Wiedemann in 1888 as light emitted from chemical reactions.

Many chemiluminescence reactions are now well known. Early studies of chemiluminescence focused primarily on the chemistry and mechanisms of chemiluminescence reactions. In the early 1960's, analytical applications of chemiluminescence reactions began to appear in the literature. Since then, chemiluminescence analytical methods have grown substantially, due to the advantages of low detection limits, wide linear dynamic ranges, and rapid response.

The early analytical applications involved manual techniques for mixing reagent and sample, and measuring the light emitted. In 1975, Ruzicka and Hansen introduced Flow Injection Analysis, which provided a new tool for performing chemiluminescence analyses. With Flow Injection Analysis, reagent and sample can be automatically mixed rapidly and reproducibly in a flowing stream, in close proximity to a chemiluminescence detector. Flow cell designs which caused reagent and sample to merge close to the light-sensing detector allowed rapid chemiluminescence chemistry to be monitored. Critical to the success of this mode of operation is rapid and efficient mixing of the components. This automation made chemiluminescence an even more attractive analytical technique.

A typical Flow Injection Analysis chemiluminescence configuration is shown in FIG. 1.

Containers of a carrier liquid 2 and of a reagent 4 are connected to a pump 8, and a sample 6 is injected into a flowing stream 2a of the carrier liquid 2. A reagent stream 4a merges at a T connection 9 with the stream 2a, which now contains the sample 6. The emerging stream 9a, now containing carrier liquid 2, reagent 4, and sample 6, flows for mixing through a mixing coil 14 into a flow cell 10, and light emitted by chemiluminescence is detected and its intensity measured by a detector 12.

In 1990 Ruzicka and Marshall introduced Sequential Injection Analysis. This method is a variant of Flow Injection Analysis which offers some important advantages. Whereas with Flow Injection Analysis the sample is injected into a flowing carrier stream, with Sequential Injection Analysis adjacent sample and reagent zones are aspirated into a holding coil, and then the flow is reversed to transport the zones to the detector. Mixing and chemical reaction between the zones occur during transport. Means have been developed to promote rapid radial mixing while minimizing axial dispersion. These means typically include pumping the zone stack through a torturous path involving rapid changes in direction of flow. Sequential Injection Analysis can be performed with simpler apparatus, and uses considerably less reagent as compared to Flow Injection Analysis.

A typical configuration of apparatus for Sequential Injection Analysis is shown in FIG. 2.

Containers of a carrier liquid 2, a reagent 4, and a sample 6 are connected to a bidirectional pump 8 through a selection valve 16 having a common port 16a, and an outlet port 18 connected to a flow cell 10. Mixing of the sample 6 and the reagent 4 occurs in a holding coil 15. Intensity of chemiluminescence is detected and measured by a detector 12.

Typically, in Flow Injection Analysis and Sequential Injection Analysis chemiluminescence systems, as well as in post-column chemiluminescence derivatization with liquid chromatography, a length of coiled tubing is used as the flow cell. A schematic representation of such a cell for Flow Injection Analysis is shown in FIG. 3. Streams 2a of sample and 4a of reagent merge in a T-connection 9 external of the coil 9a, which initiates mixing, and the reaction mixture flows through the coil 9a, emitting light which is captured by a detector 12. After flowing through the coil 9a, the mixture is discharged to waste via a tube 18.

While this type of simple flow-through cell works well, it has a number of shortcomings that impact its performance; viz.:

(a) Only a coil configuration is practical. Other flow paths, such as reversing turns which enhance mixing, are not possible or easily achieved. While mixing is initiated in the T-connection 9, it is not complete, and further but still incomplete mixing occurs during transit of the reacting zones through the coil 9a.

(b) Mixing is initiated external to the coil 9a where no light is captured; so for very fast reactions, especially with rapid decay of the chemiluminescence, some of the emitted light is lost prior to detection.

(c) Commonly-used polymeric tubing is not completely transparent; it is generally translucent. Hence, some light is lost in the tubing walls.

(d) Tubing has a curved wall, which causes light loss due to reflection, compared with a flat wall.

(e) The internal diameter of the channel is limited by the availability of tubing sizes.

The present invention provides a flow cell which eliminates all of the limitations of the coiled tube, and is thus more efficient at generating and transmitting light produced by chemiluminescence.

SUMMARY OF THE INVENTION

In general, the present invention in a first aspect provides a flow cell for chemiluminescence analysis. The flow cell comprises (a) a flat thin plate having first and second faces, and having a groove in the first face of the plate; (b) a flat window having first and second faces, the plate and the window forming a flow channel in the groove in the first face of the plate when the first face of the plate is pressed against the first face of the window, the flow channel having first and second walls, the first wall being the first face of the plate, the second wall being the first face of the window; (c) an inlet port for the groove, that penetrates through the plate; (d) an outlet port for the groove, that penetrates through the plate; and (e) means for measuring chemiluminescence emitted from the flow cell.

In a second aspect, the invention provides an improvement in a flow cell for use with flow-based chemiluminescence measurements. The improvement comprises using a plate with grooves, the plate having a pair of converging inlet ports near the center of the plate, to provide a mechanism for mixing a sample and a reagent, thereby effecting immediate generation of chemiluminescence in the path of means for measuring chemiluminescence emitted from the flow cell.

DETAILED DESCRIPTION OF THE DISCLOSED EMBODIMENTS

Figure 1:
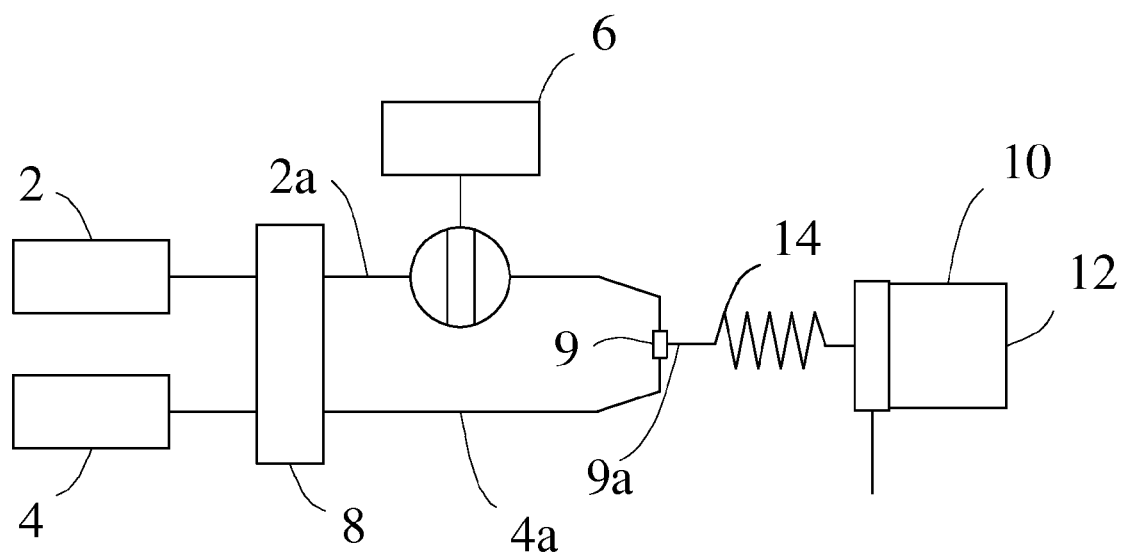
FIG. 1 is a prior-art configuration for Flow Injection Analysis.
Figure 2:
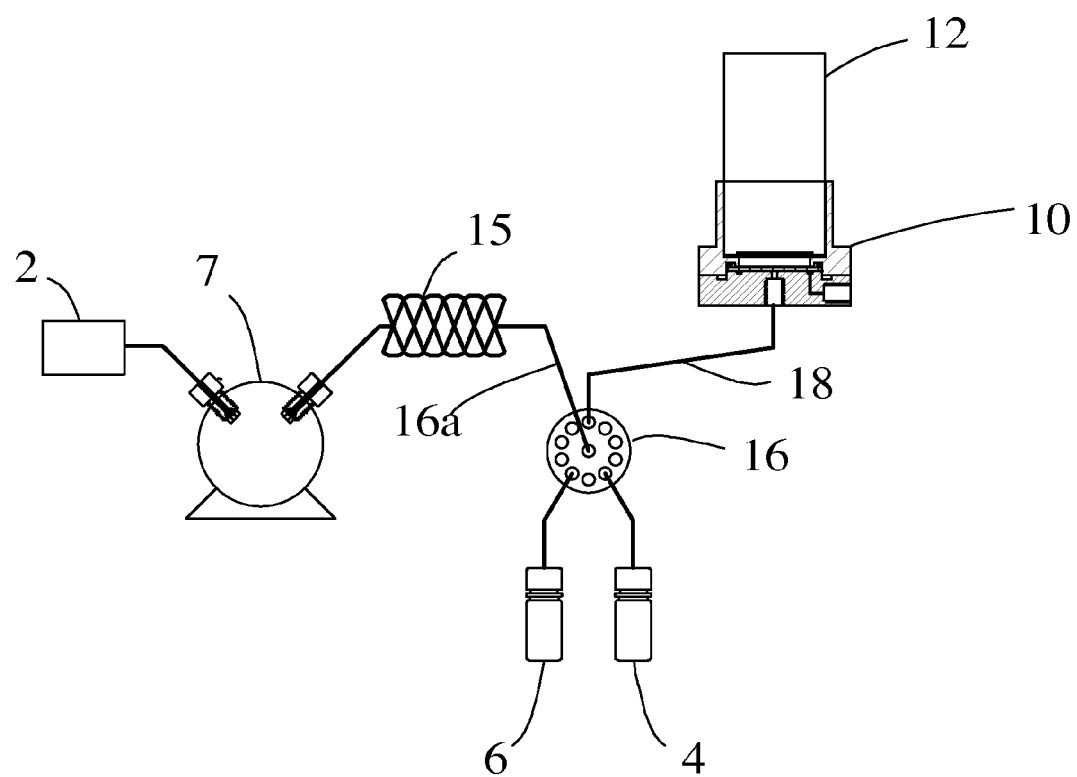
FIG. 2 is a prior-art configuration of apparatus for Sequential Injection Analysis.
Figure 3:
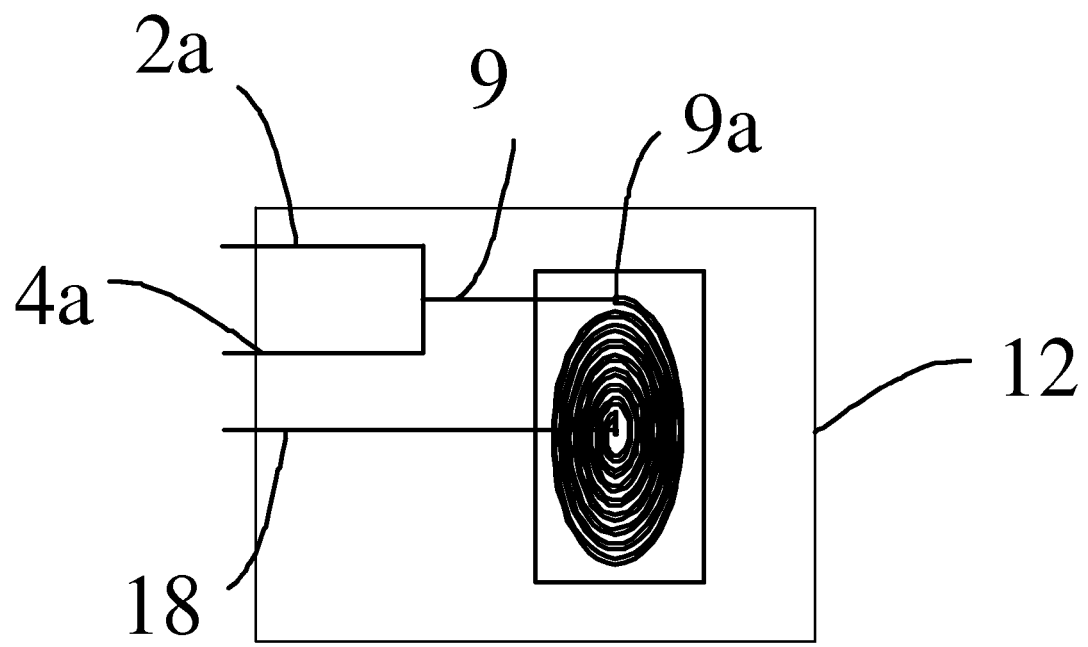
FIG. 3 is a schematic representation of a cell for Flow Injection Analysis using a length of coiled tubing as the flow cell.
Figure 4:
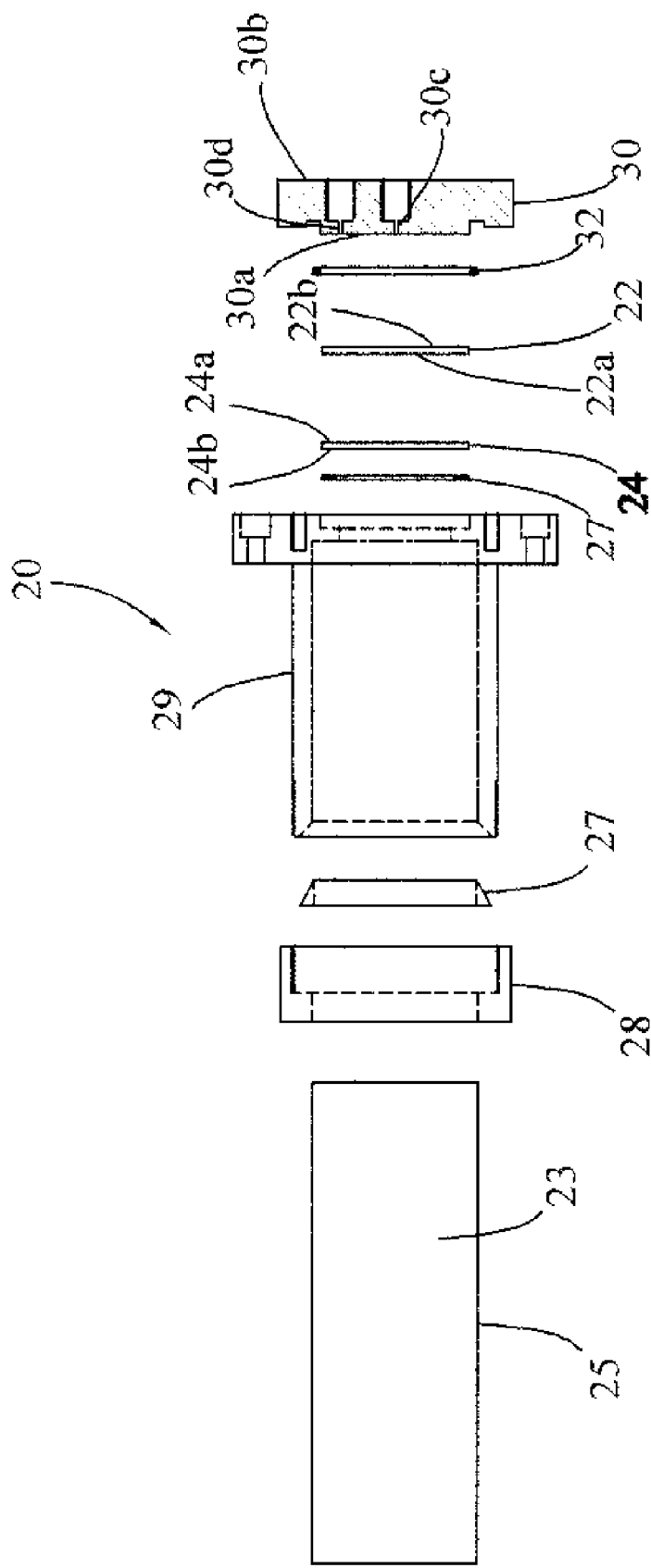
FIG. 4 is an exploded view of a flow cell for chemiluminescence analysis, made in accordance with the principles of the present invention.
Figure 5A:
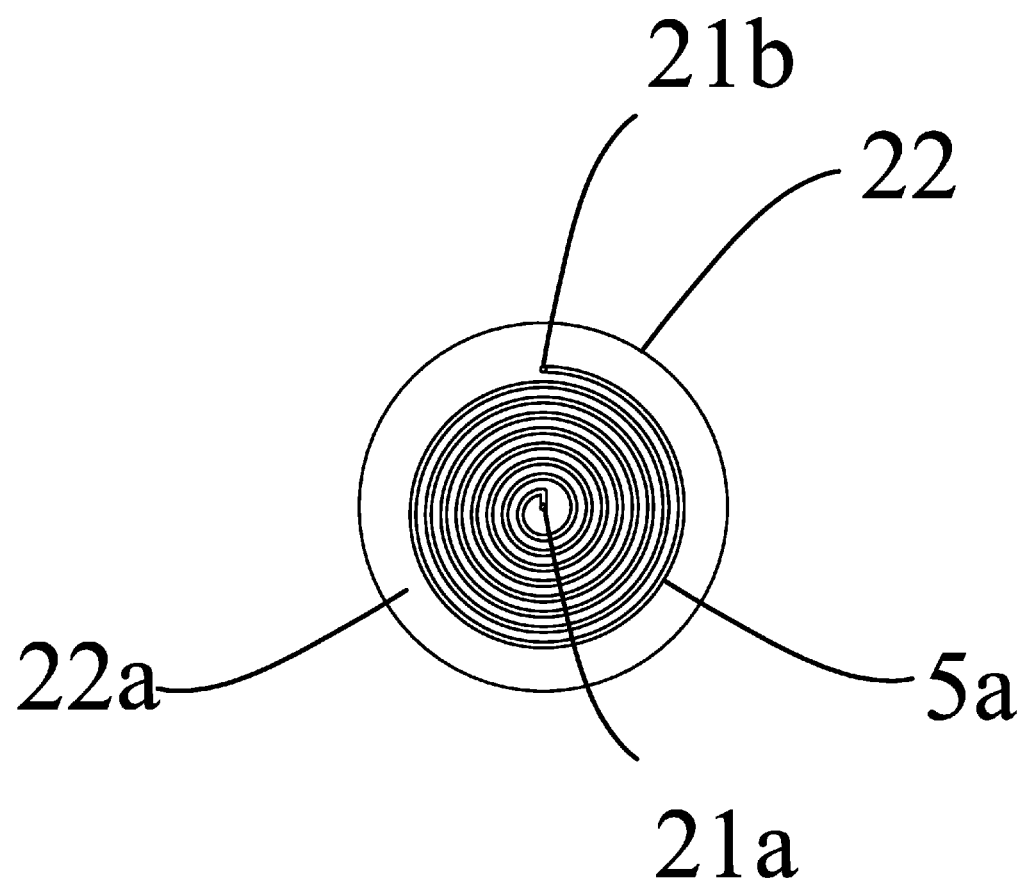
FIGS. 5A-5F are schematic representations of various embodiments of a portion of a flow cell shown in FIG. 4.
Figure 5B:
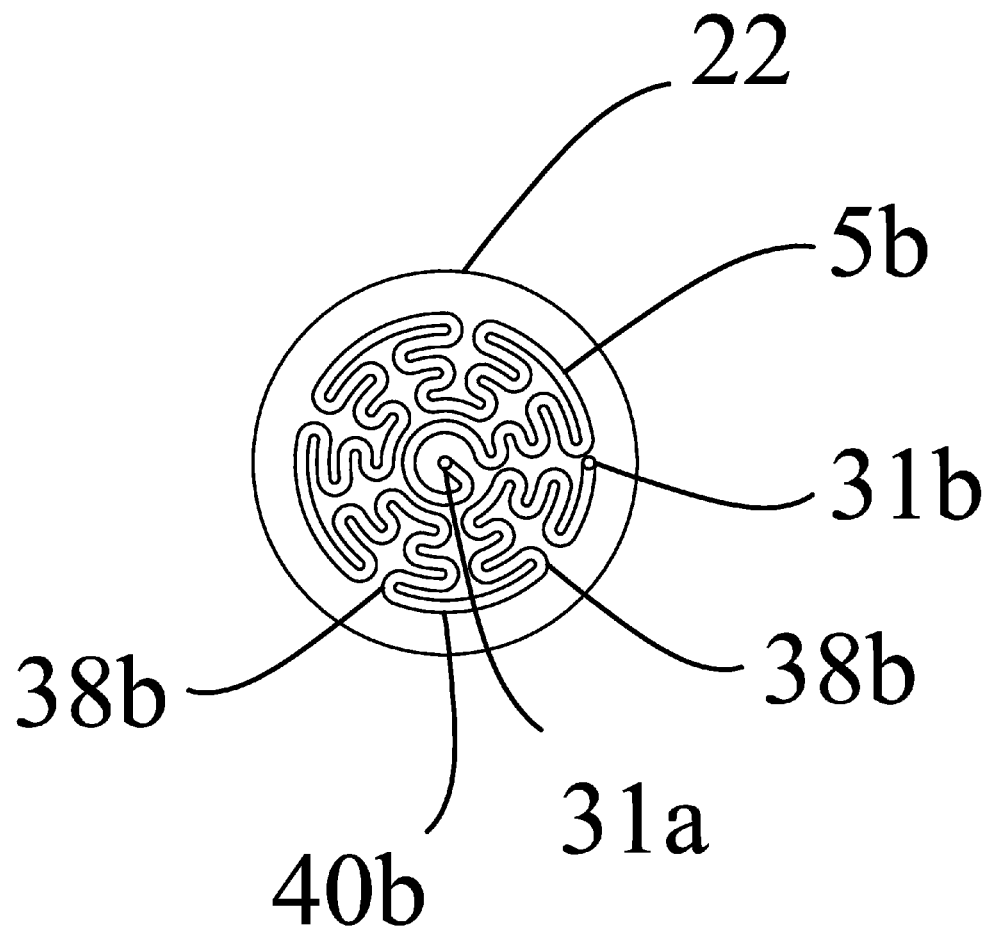
Figure 5C:
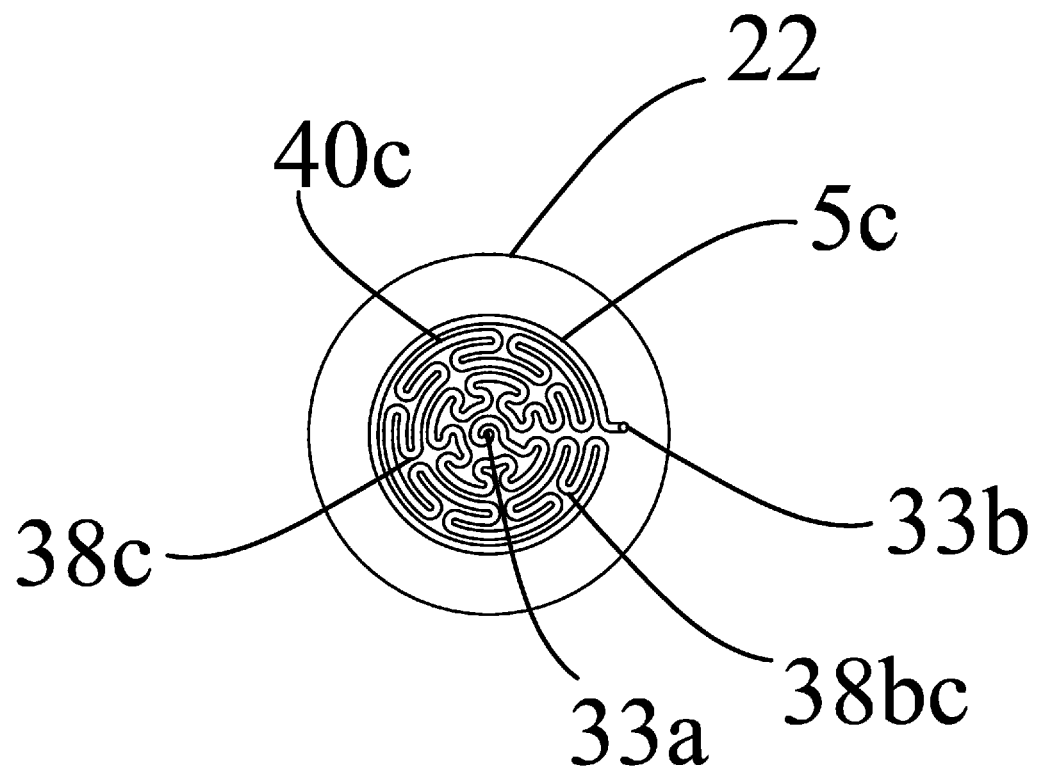
Figure 5D:
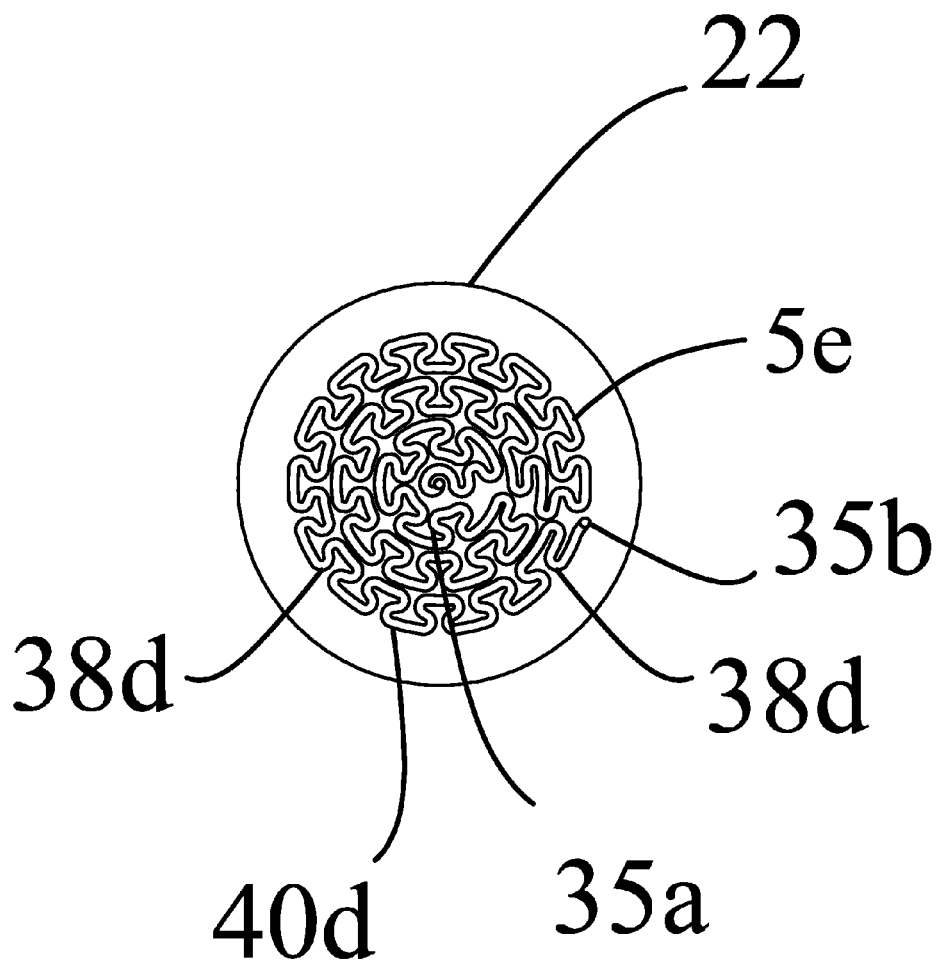
Figure 5E:
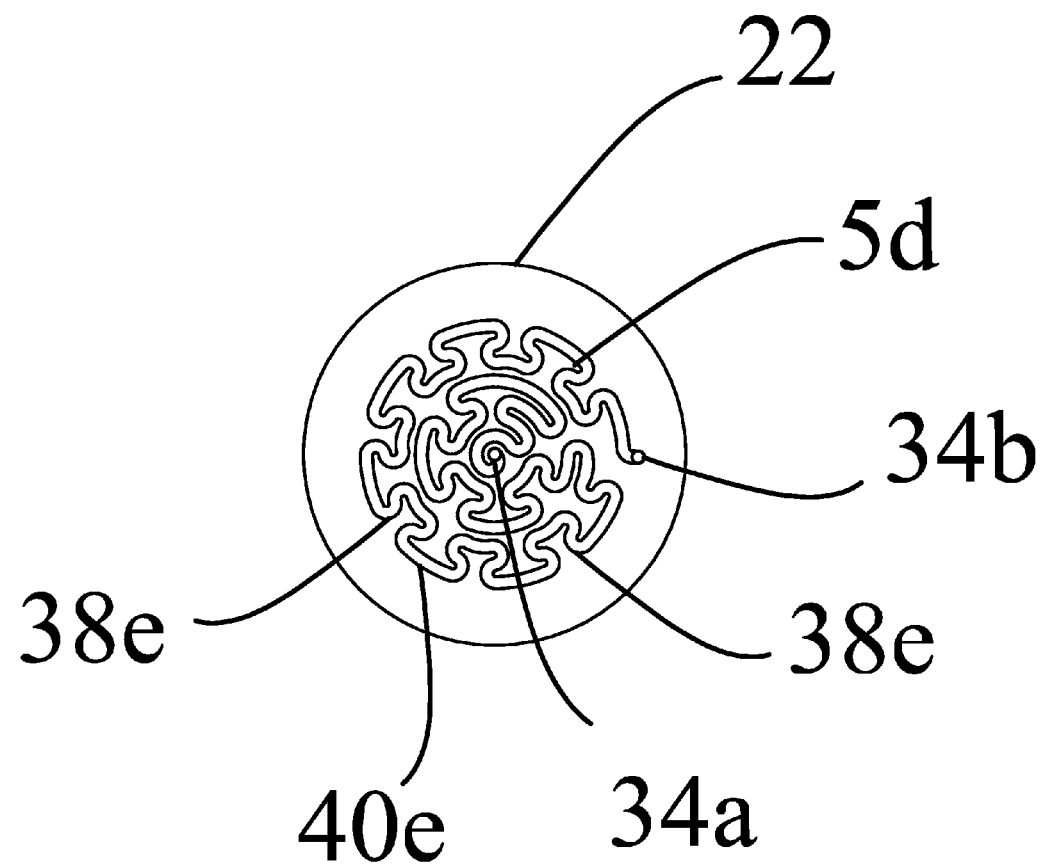
Figure 5F:
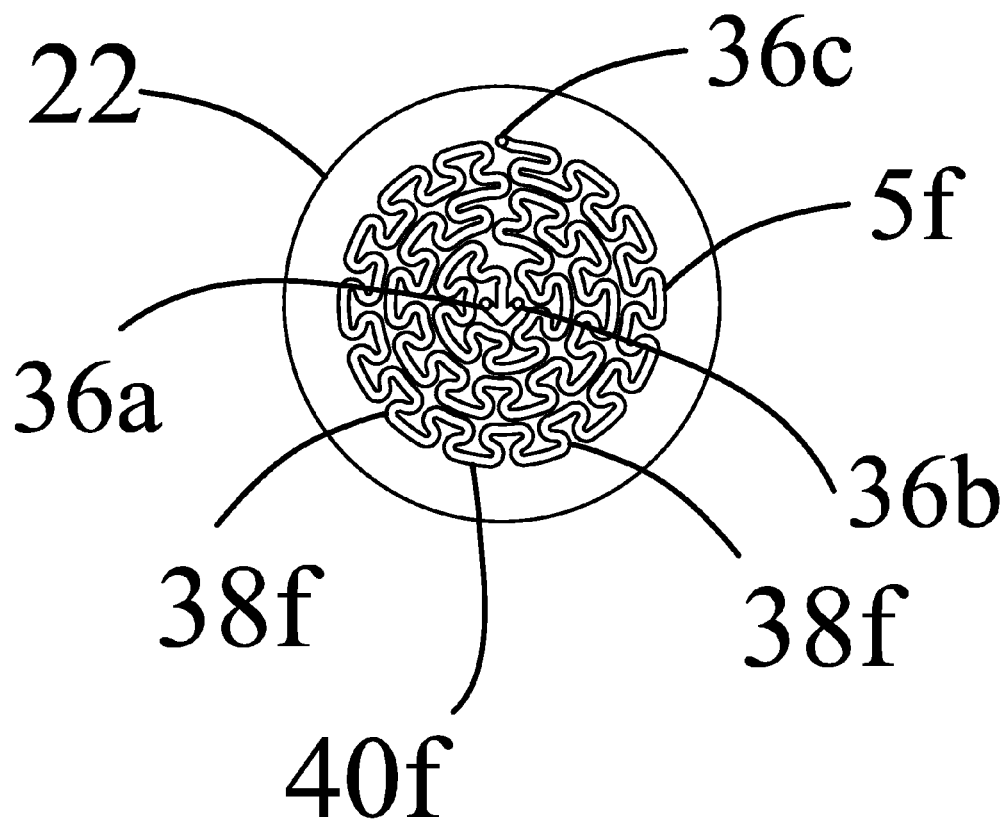

More specifically, reference is made to FIG. 4, in which is shown a flow cell for chemiluminescence analysis, made in accordance with the principles of the present invention, and generally designated by the numeral 20.

The flow cell 20 comprises a flat, thin plate 22 having first and second opposite faces 22a and 22b. There is a flat sapphire window 24 having first and second opposite faces 24a and 24b. In lieu of the sapphire window, quartz, glass, or other acceptable materials may be employed. By "acceptable" is meant "maximally transparent in wavelength range of emission of the emitted light and chemically resistant to the reagents used". An example would be emitted radiation in the "visible" region of the light spectrum. Sapphire, quartz and glass would all be acceptable. However, with emitted radiation in the "ultraviolet" spectral region, glass would no longer be acceptable, due to limited light transmission. A light detector 23 such as a circular photomultiplier, photon counter, or photodiode is used to detect and measure chemiluminescence emitted from the flow cell 20.

A housing for the plate 22, the sapphire window 24, and the detector 23 comprises a body 29, and a cap 30 having first and second opposite faces 30a and 30b. An O-ring 32 is disposed between the plate 22 and the cap 30. A flat gasket 27 is beneficially disposed between the cap 30 and the body 29 of the housing. The light detector 23 is connected to the housing body 29 via an end cap 28 and a ferrule 27, which grips the barrel 25 of the light detector 23, to lock the barrel 25 into place in a way to minimize the ingress of ambient light.

Reference is now made to FIGS. 5A-5F, in which are shown various embodiments of the plate 22. Groove 5a, FIG. 5A, has an inlet port 21a, and an outlet port 21b. Groove 5b, FIG. 5B, has an inlet port 31a and an outlet port 31b. Groove 5c, FIG. 5C, has an inlet port 33a and an outlet port 33b. Groove 5d, FIG. 5D, has an inlet port 34a and an outlet port 34b. Groove 5e, FIG. 5E, has an inlet port 35a and an outlet port 35b. Groove 5f, FIG. 5F, has a pair of inlet ports 36a, 36b, and an outlet port 36c. The preferred material of construction of the plate 22 is polytetrafluoroethylene, but other materials are suitable. By "suitable" is meant "resistant to chemicals with which it would be in contact".

The plate 22 and the sapphire window 24 form therebetween a flow channel in each of the grooves 5a, 5b, 5c, 5d, 5e, and 5f when the first face 22a of the plate 22 is pressed against the first face 24a of the sapphire window 24. The first face 22a of the plate 22 constitutes a first wall of the flow channel, and the first face 24a of the sapphire window constitutes a second wall of the flow channel.

The advantages of the flow cell 20 of the present invention over flow cells of the prior art will now be apparent to those skilled in the art.

The channel wall through which chemiluminescent light is transmitted to the detector 23 is a flat transparent surface having a high efficiency of light transmission relative to a curved, translucent polymeric wall.

A wide variety of flow-path dimensions and configurations tailored to a particular application can be designed and machined. The grooves 5b to 5f shown in FIGS. 5B-5F have a plurality of loops comprising pairs of oppositely-directed horseshoe-shaped curves 38b-38f connected to one another by lateral segments 40b-40f, disposed along the grooves 5b-5f, to provide more efficient mixing of reagent and sample. The channel configuration can be easily and quickly changed, by exchanging a plate 22 with another plate having the chosen configuration.

The embodiment of the plate 22 having the groove 5f provided with a pair of converging inlet ports 36a, 36b, has the additional important advantage of internal mixing of sample and reagent in the direct path of the detector 23, thereby eliminating the need for external mixing in a conventional coiled-tubing cell. This important feature allows very fast chemiluminescence reactions to be measured without loss of emitted light during the early stages of a chemiluminescence reaction. While only two streams are indicated as merging in the groove 5f, in practice any number of inlet ports to the flow channel could be added downstream, limited only by the dimensions of the inlet fittings and of the cell.

Returning now to FIG. 4, the inlet and outlet ports pass through the transparent plate 22, and mate with inlet and outlet ports 30c and 30d in the cap 30. The ports 30c and 30d are beneficially machined to accept tubing fittings such as ¼-28 or 6-40.

While certain details and embodiments have been described to illustrate the principles of the present invention, it will be apparent to those skilled in the art that many modifications are possible within the scope of the claimed invention.

We claim:

1. A flow cell for use with flow-based chemiluminescence measurements, the flow cell comprising:
    (a) a flat thin plate having first and second faces, and having a groove in the first face of the plate, the groove having first and second ends;
    (b) a flat window having first and second faces, the plate and the window forming a flow channel in the groove in the first face of the plate when the first face of the plate is pressed against the first face of the window, the flow channel having first and second end walls, the first wall being the first face of the plate, the second wall being the first face of the window;
    (c) an inlet for the groove at the first end of the groove in the first face of the plate, the inlet port penetrating through the plate, the groove having a plurality of loops formed between the first and second ends, each loop comprising a pair of oppositely-directed horseshoe-shaped curves connected to one another by a segment lateral to the pair of oppositely-directed horseshoe-shaped curves, to enhance mixing of a sample and a reagent, and thereby increase generating and emission of chemiluminescence;
    (d) an outlet for the groove at the second end of the groove in the first face of the plate, the outlet penetrating through the plate; and
    (e) a light detector disposed in a path of the chemiluminescence generated in and emitted from the groove of the flow cell.

2. The flow cell of claim 1, wherein the first end of the groove is at a center of the window, to provide immediate generation of chemiluminescence at a center of a path from the window to the light detector, and to thereby increase sensitivity of light detection.

3. The flow cell of claim 1, wherein the flow channel comprises a series interconnection of mixing elements in which mixing is generated by reversals of flow as the flow changes from clockwise to counterclockwise rotation and from counterclockwise to clockwise rotation.

4. A flow cell for use with flow-based chemiluminescence measurements, the flow cell comprising:
  (a) a flat thin plate having first and second faces, and having a groove in the first face of the plate, the groove having first and second ends;
  (b) a flat window having first and second faces, the plate and the window forming a flow channel in the groove in the first face of the plate when the first face of the plate is pressed against the first face of the window, the flow channel having first and second walls, the first wall being the first face of the plate, the second wall being the first face of the window;
  (c) first and second inlets for the groove for a sample and a reagent, respectively, at the first end of the groove in the first face of the plate, the inlets being directly opposite one another, penetrating through the plate on opposite sides of the groove, and converging in the groove to provide a mechanism for mixing the sample and the reagent, and to provide immediate generation and emission of chemiluminescence, the groove having a plurality of loops disposed along the groove, each loop comprising a pair of oppositely-directed horseshoe-shaped curves connected to one another by a segment lateral to the pair of oppositely-directed horseshoe-shaped curves, to enhance the mixing of the sample and the reagent and thereby increase the generation and emission of the chemiluminescence;
  (d) an outlet for the groove at the second end of the groove in the first face of the plate, the outlet penetrating through the plate; and
  (e) a light detector disposed in path of the chemiluminescence generated in and emitted from the groove of the flow cell.

5. The flow cell of claim 4, wherein the first end of the groove is at a center of the window, to provide immediate generation of chemiluminescence at a center of a path from the window to the light detector, and to thereby increase sensitivity of light detection.

6. The flow cell of claim 4, wherein the flow channel comprises a series interconnection of mixing elements in which mixing is generated by reversals of flow as the flow changes from clockwise to counterclockwise rotation and from counterclockwise to clockwise rotation.

* * * * *